United States Patent [19]
Takita et al.

[11] 4,377,594
[45] Mar. 22, 1983

[54] DERIVATIVE OF 4-(N-(SUBSTITUTED-BENZYLIDENE)AMINO-METHYL CYCLOHEXANE-1-CARBOXYLIC ACID

[75] Inventors: Hitoshi Takita; Yutaka Mukaida; Sakuo Noda; Hidetoshi Kobayashi, all of Tokyo, Japan

[73] Assignee: Kureha Kagaku Kogyo Kabushiki Kaisha, Tokyo, Japan

[21] Appl. No.: 267,249

[22] Filed: May 26, 1981

[30] Foreign Application Priority Data

Jun. 4, 1980 [JP] Japan .................................. 55-75055
Jan. 9, 1981 [JP] Japan .................................... 56-1790

[51] Int. Cl.³ .................. C07C 101/30; A61K 31/195
[52] U.S. Cl. .................................... 424/309; 424/319; 560/35; 562/440
[58] Field of Search .................. 560/35; 424/309, 319; 562/440, 451

[56] References Cited

U.S. PATENT DOCUMENTS 3,563,923  2/1971  Buss et al. .............................. 560/35
3,697,589  10/1972 Menasse et al. ...................... 562/440
4,071,686  1/1978  van Dyk et al. ..................... 562/440

Primary Examiner—James H. Reamer
Attorney, Agent, or Firm—Wegner & Bretschneider

[57] ABSTRACT

A novel compound of 4-[N-(substituted-benzylidene)aminomethyl]cyclohexane-1-carboxylic acid or a salt or an ester thereof which has specific pharmacologic activities, a method for preparing thereof and a pharmaceutical composition comprising thereof as an active ingredient are provided.

13 Claims, 1 Drawing Figure

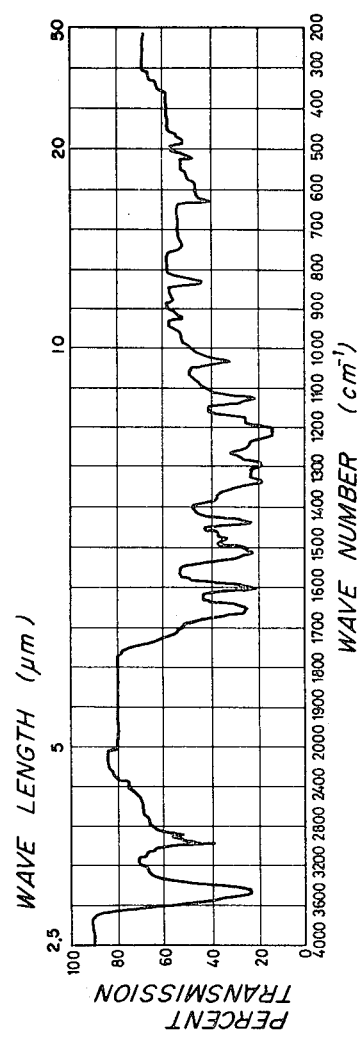

DERIVATIVE OF 4-(N-(SUBSTITUTED-BENZYLIDENE)AMINO-METHYL CYCLOHEXANE-1-CARBOXYLIC ACID

This invention relates to a novel derivative of 4-[N-(substituted-benzylidene)aminomethyl]cyclohexane-1-carboxylic acid, a method for preparing thereof and a pharmaceutical composition comprising thereof.

It is an object of the invention to provide a novel compound of 4-[N-(substituted-benzylidene)aminomethyl]cyclohexane-1-carboxylic acid or a salt or an ester thereof. An another object of the invention is to provide a method for preparing the novel compound. Furthermore, still another object is to provide a pharmaceutical composition comprising a pharmaceutically effective amount of the novel compound as an active ingredient.

The novel compound of 4-[N-(substituted-benzylidene) aminomethyl]cyclohexane-1-carboxylic acid (hereinafter referred to as the compound of the invention) is represented by the general formula (I):

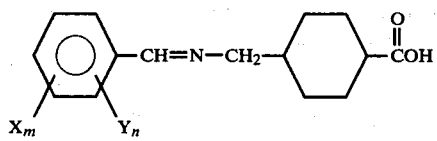

wherein X is hydroxyl- or methoxy group, Y is hydrogen or hydroxyl- or methoxy group, m and n are integer and the sum of m and n is equal to or less than 5, provided that 4-[N-3',4'-dihydroxybenzylidene)aminomethyl]cyclohexane-1-carboxylic acid is not included in the general formula (I). In the general formula (I), the cyclohexane ring includes both trans- and cis form, and X and Y may be different or same.

The compound of the invention includes salt or ester derivatives. The salt is an alkali or alkaline earth metal salt such as sodium salt, potassium salt, calcium salt, magnesium salt, etc., ammonium salt or primary-, secondary-, tertiary- or quaternary ammonium salt. The ester is a lower alkyl ester of which an alkyl group has 1 to 3 carbon atoms, such as methyl-, ethyl- or n- or isopropyl group.

The compound of the invention is preferably prepared by the method described below, although it may be prepared by the conventional method. Namely, a compound of substituted benzaldehyde represented by the general formula (II)

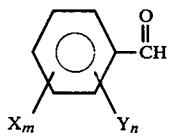

wherein X, Y, m and n are the same as in the general formula (I), is brought into reaction with 4-aminomethyl-cyclohexane-1-carboxylic acid represented by the formula (III):

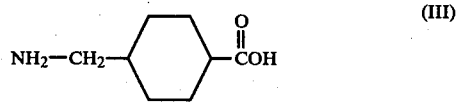

wherein the cyclohexane ring includes both trans- and cis form, or a lower alkyl ester thereof, and the compound of the invention (acid- or ester form) represented by the general formula (I) is obtained by dehydrating-condensation reaction.

The reaction between the compound of the formula (II) and the compound of the formula (III) or an ester thereof is carried out in an organic solvent at lower than 150° C., preferably 0° to 120° C. under atmospheric inert gas. At higher than 150° C., the yield of the desired product is reduced because of various side reactions. Any organic solvent may be used for the reaction if it does not participate in the reaction. A lower alcohol such as methanol or ethanol, benzene, toluene, dimethyl- formamide, acetonitrile or the like is conventionally used for the reaction.

Since the reaction takes place together with dehydrating, the reaction is carried out in the presence of a dehydrating agent or while removing water formed by the reaction under the reflux of the solvent. An anhydride of a lower alcohol such as an anhydrous methanol or ethanol can be used for the solvent and at the same time for the dehydrating agent.

The compound of the invention (acid- or ester form) is isolated by treating the reaction mixture with a known method after the reaction.

The compound of the invention of salt form is prepared by the conventional method for neutralization by using a base such as hydroxide, carbonate or bicarbonate of an alkali or alkaline earth metal, for example, sodium, potassium, calcium or magnesium, etc., ammonia or primary-, secondary- or tertiary amine or quaternary ammonium salt. For example, a sodium salt is obtained by neutralizing the compound of the invention (an acid form) obtained by the above-mentioned reaction with an alcoholic- or aqueous solution of sodium hydroxide under atmospheric inert gas at lower than 100° C., usually at 0° to 50° C.

The method mentioned above is only an embodiment of the method for preparing the compound of the invention, and the method of the invention is not restricted to the method as above.

The compound of the invention shows an inhibitory effect on platelet aggregation and/or polynuclear leukocyte migration, and a low acute toxicity, as will be shown in Example 10. Accordingly, the compound of the invention is useful as a remedy for various diseases, such as inflammation, thrombosis, encephalorrhagia, hypertension, asthma or cancer, etc., especially for chronic diseases such as rheumatism or systemic lupus erythematosus (SLE), etc.

When the compound of the invention is used for a pharmaceutics, the salt or ester must be pharmaceutically acceptable.

Furthermore, the compound of the invention may be used as an active ingredient of a pharmaceutical composition for the above-mentioned diseases.

The compound of the invention can be administered perorally, rectally or through injection in the various dosage forms as a composition together with a pharmaceutically acceptable carrier and/or an adjuvant. In these cases, a mixture of two or more kinds of the compound of the invention or a mixture together with other pharmaceutically active materials may be used as an active ingredient of a pharmaceutical composition.

The dosage form of the composition may be tablet, sublingual tablet, powder, capsule, troch, aqueous or oily solution, suspension, emulsion, syrup, aqueous or oily injection. An example of the carrier mentioned above is water, gelatin, lactose, starch, pectin, magnesium stearate, stearic acid, talc, vegetable oil, gum arabic, polyalkylene glycol, vaseline, sorbitan tri-oleate, polyoxyethylene-sorbitan mono-oleate, alkylphenol, aliphatic alcohols, polyvinyl pyrrolidone, or the like. In the composition, if necessary, edulcorant, flavor, tinctorial agent, preservative, salt for osmoregulation or buffer, that is, the conventional pharmaceutical adjuvant may be used together.

The content of the compound of the invention in the pharmaceutical composition may be adequately varied, however, it is 0.01%–100% by weight preferably 0.05%–80% by weight of the composition.

The pharmaceutical composition of the invention is administered into a human or animal parenterally, for example, rectally, through injection (hypodermic, intramuscular or intravenous, or drip), preferably perorally (for example sublingual etc.).

A dose of the pharmaceutical composition of the invention is 0.1 to 500 mg, preferably 0.5 to 200 mg per day per one kilogram of the body weight in the case of peroral administration into a human, and 0.01 to 200 mg, preferably 0.1 to 100 mg in the case of parenteral administration, and the pharmaceutics is administered one to four times a day. However the dose of the pharmaceutical composition depends on age, individuality, condition of a disease etc. of a human or animal, and the dose out of the above-mentioned range may be used.

The properties, method for preparation and pharmacologic effects of the compound of the invention are concretely described while referring to the examples.

EXAMPLE 1

Preparation of trans-4-[N-(2'-hydroxybenzylidene)aminomethyl]cyclohexane-1-carboxylic acid Into 30 ml of dehydrated and purified methanol, 1.550 g (12.7 m mol) of 2-hydroxybenzaldehyde was dissolved, and the resulting solution was dropped into 1.994 g (12.7 m mol) of trans-4-aminomethyl-cyclohexane-1-carboxylic acid under atmospheric nitrogen, and the resulting mixed solution was refluxed while stirring for 3 hours. After cooling the reaction mixture to room temperature, the deposited yellow crystal was filtered, washed with methanol and vacuum-dried. 2.62 g of trans-4-[N-(2'-hydroxybenzylidene)aminomethyl]cyclohexane-1-carboxylic acid was obtained with the yield of 83.6%.

The characteristics of the compound of the invention thus obtained were as follows:

(1) fusing point; 151°–153° C., measured by Capillary Method

| | (2) elementary analysis; | | |
|---|---|---|---|
| | C (%) | H (%) | N (%) |
| theoretical: | 68.94 | 7.33 | 5.36 |
| experimental: | 69.1 | 7.2 | 5.4 |

(3) nuclear magnetic resonance (NMR) spectrum in dimethylsulfoxide;

$\delta = 0.95$–$2.0$ (9H, m), 2.0–2.15 (1H), 3.45 (2H, d), 6.65 (1H), 6.94 (1H), 7.30 (1H), 7.42 (1H), 8.50 (1H), 13.0 (1H).

EXAMPLE 2

Preparation of sodium trans-4-[N-(2'-hydroxybenzylidene)aminomethyl]cyclohexane-1-carboxylate Into 50 ml (5 m mol) of 0.1 N aqueous solution of sodium hydroxide, 1.305 g (5 m mol) of trans-4-[N-(2'-hydroxybenzylidene)aminomethyl]cyclohexane-1-carboxylic acid obtained in Example 1 was added under atmospheric nitrogen, and the resulting mixture was stirred for 2 hours at room temperature to obtain a yellow solution. The yellow solution was filtered and then freeze-dried, and 1.42 g of sodium trans-4-[N-(2'-hydroxybenzylidene)aminomethyl]cyclohexane-1-carboxylate was obtained.

The characteristics of the sodium salt thus obtained were as follows:

(1) melting point; higher than 230° C., measured by Capillary Method

| | (2) elementary analysis: | | |
|---|---|---|---|
| | C (%) | H (%) | N (%) |
| theoretical: | 64.63 | 6.78 | 4.71 |
| experimental: | 64.0 | 6.9 | 4.9 |

(3) Infrared (IR) absorption spectrum:

$\nu(cm^{-1}) = 3400, 2920, 1633, 1620, 1580, 1540, 1500, 1420, 1290, 1048, 858, 752.$

EXAMPLE 3

Preparation of trans-4-[N-(4'-hydroxybenzylidene)aminomethyl]cyclohexane-1-carboxylic acid The reaction of 1.550 g (12.7 m mol) of 4-hydroxybenzaldehyde with 1.994 g (12.7 m mol) of trans-4-aminomethyl-cyclohexane-1-carboxylic acid was carried out while refluxing for 5 hours according to the method of Example 1, and 1.26 g of trans-4-[N-(4'-hydroxybenzylidene)aminomethyl]cyclohexane-1-carboxylic acid was obtained in the form of orange crystal with the yield of 38.0%.

The characteristics of the compound of the invention thus obtained were as follows:

(1) melting point: 208° C. with decomposition, measured by Capillary Method

| | (2) elementary analysis; | | |
|---|---|---|---|
| | C (%) | H (%) | N (%) |
| theoretical: | 68.94 | 7.33 | 5.36 |
| experimental: | 69.0 | 7.1 | 5.50 |

(3) NMR spectrum;

$\delta = 0.9$–$2.0$ (9H, m), 2.1–2.2 (1H), 3.35 (2H, d), 6.80 (2H, d), 7.55 (2H, d), 8.12 (1H, s).

EXAMPLE 4

Preparation of trans-4-[N-(2',3'-dihydroxybenzylidene)aminomethyl]-cyclohexane-1-carboxylic acid and sodium salt thereof The reaction of 1.753 g (12.7 m mol) of 2,3-dihydroxybenzaldehyde with 1.994 g (12.7 m mol) of trans-4-aminomethylcyclohexane-1-carboxylic acid was carried out according to the method of Example 1, and 2.53 g of trans-4-[N-(2',3'-dihydroxybenzylidene)aminomethyl]-cyclohexane-1-carboxylic acid was obtained in the form of yellow crystal with the yield of 71.9%.

The characteristics of the compound of the invention thus obtained were as follows:

(1) melting point; 190°–192° C., measured by Capillary Method

| | (2) elementary analysis; | | |
|---|---|---|---|
| | C (%) | H (%) | N (%) |
| theoretical: | 64.97, | 6.91, | 5.05, |
| experimental: | 64.6, | 6.9, | 4.9, |

(3) NMR spectrum;

$\delta = 0.97$–2.00 (9H, m), 2.15 (1H), 3.65 (2H, d), 4.04 (2H), 6.53–6.88 (3H), 8.45 (1H).

Furthermore, the compound of the invention thus obtained was neutralized by the equivalent sodium hydroxide to obtain sodium trans-4-[N-(2',3'-dihydroxybenzylidene)aminomethyl]cyclohexane-1-carboxylate.

EXAMPLE 5

Preparation of trans-4-[N-(2',4'-dihydroxybenzylidene)aminomethyl]-cyclohexane-1-carboxylic acid The reaction of 1.753 g (12.7 m mol) of 2,4-dihydroxybenzaldehyde with 1.994 g (12.7 m mol) of trans-4-aminomethylcyclohexane-1-carboxylic acid was carried out according to the method of Example 1, and 3.02 g of trans-4-[N-(2',4'-dihydroxybenzylidene)aminomethyl]-cyclohexane-1carboxylic acid was obtained in the form of orange-yellow crystal with the yield of 85.8%.

The characteristics of the compound of the invention thus obtained were as follows:

(1) melting point; 225° C. with decomposition, measured by Capillary Method

| | (2) elementary analysis; | | |
|---|---|---|---|
| | C (%) | H (%) | N (%) |
| theoretical: | 64.97, | 6.91, | 5.05, |
| experimental: | 64.5, | 7.1, | 5.3 |

(3) NMR spectrum;

$\delta = 1.06$–1.85 (9H, m), 2.01 (1H), 2.52 (2H), 3.39 (2H), 6.17 (1H), 6.28 (1H), 7.17 (1H), 8.29 (1H), 10–12 (1H).

EXAMPLE 6

Preparation of trans-4-[N-(2'-methoxybenzylidene)aminomethyl]cyclohexane-1-carboxylic acid and sodium salt thereof The reaction of 1.727 g (12.7 m mol) of 2-methoxybenzaldehyde with 1.994 g (12.7 m mol) of trans-4-aminomethylcyclohexane-1-carboxylic acid was carried out according to the method of Example 1, and 2.21 g of trans-4-[N-(2'-methoxybenzylidene) aminomethyl]cyclohexane-1-carboxylic acid in the form of colorless crystal with the yield of 63.3%.

The characteristics of the compound of the invention thus obtained were as follows:

(1) melting point; 174°–175° C., measured by Capillary Method

| | (2) elementary analysis; | | |
|---|---|---|---|
| | C (%) | H (%) | N (%) |
| theoretical: | 69.79, | 7.69, | 5.09 |
| experimental: | 69.7, | 7.9, | 5.2 |

(3) NMR spectrum;

$\delta = 0.90$–1.98 (9H, m), 2.10 (1H), 3.49 (2H, d), 3.83 (3H, s), 6.99 (1H), 7.22 (1H), 7.46 (1H), 7.83 (1H), 8.58 (1H).

Besides, sodium salt of the compound of the invention thus obtained was prepared by neutralizing with equivalent sodium hydroxide, and sintered at about 170° C.

EXAMPLE 7

Preparation of trans-4-[N-(3',4'-dimethoxybenzylidene)aminomethyl]-cyclohexane-1-carboxylic acid The reaction of 2.12 g (12.72 m mol) of 3,4-dimethoxybenzaldehyde with 2.00 g (12.72 m mol) of trans-4-aminomethylcyclohexane-1-carboxylic acid was carried out in methanol according to the method of Example 1, and 2.45 g of trans-4-[N-(3',4'-dimethoxybenzylidene)aminomethyl]cyclohexane-1-carboxylic acid in the form of colorless flake-crystal with the yield of 63.1%.

The characteristics of the compound of the invention thus obtained were as follows:

(1) melting point; 196°–199° C., measured by the Hot-Plate Method

| | (2) elementary analysis; | | |
|---|---|---|---|
| | C (%) | H (%) | N (%) |
| theoretical: | 66.86, | 7.59, | 4.59, |
| experimental: | 66.6, | 7.5, | 4.6. |

(3) NMR spectrum;

$\delta = 1.02$–1.83 (9H, m), 1.90–2.18 (1H), 3.37 (2H, d), 3.79 (6H, s), 6.99 (1H, d), 7.24 (1H, d), 7.34 (1H, s), 8.17 (1H, s).

EXAMPLE 8

Preparation of trans-4-[N-(3',4',5'-trimethoxybenzylidene)aminomethyl]cyclohexane-1-carboxylic acid The reaction of 2.49 g (12.72 m mol) of 3,4,5-trimethoxybenzaldehyde with 2.00 g (12.72 m mol) of trans-4-aminomethylcyclohexane-1-carboxylic acid was carried out in 60 ml of methanol while refluxing for 6.5 hours, according to the method of Example 1, and 3.32 g of trans-4-[N-(3',4',5'-trimethoxybenzylidene)aminomethyl]cyclohexane-1-carboxylic acid in the form of colorless needle-crystal with the yield of 77.8%.

The characteristics of the compound of the invention thus obtained were as follows:

(1) melting point; 176°–180° C., measured by the Hot-Plate Method

|  | (2) elementary analysis; | | |
|---|---|---|---|
|  | C (%) | H (%) | N (%) |
| theoretical: | 64.46, | 7.51, | 4.18, |
| experimental: | 64.3, | 7.5, | 4.1. |

(3) NMR spectrum;

$\delta = 1.00-1.90$ (9H, m), 2.00–2.15 (1H), 3.40 (2H, d), 3.70 (3H, s), 3.81 (6H, s), 7.06 (2H, s), 8.18 (1H, s).

EXAMPLE 9

Preparation of trans-4-[N-(3'-methoxy-4'-hydroxybenzylidene)aminomethyl]cyclohexane-1-carboxylic acid The reaction of 12.7 m mol of 3-methoxy-4-hydroxybenzaldehyde with 12.7 m mol of trans-4-aminomethyl-cyclohexane-1-carboxylic acid was carried out in 60 ml of methanol for 10 hours according to the method of Example 1. The reaction solution was filtered and methanol was evaporated off at 110° to 120° C. under reduced pressure for 5 hours. The yellow powder of trans-4-[N-(3'-methoxy-4'-hydroxybenzylidene)aminomethyl]cyclohexane-1-carboxylic acid was obtained with the yield of 80.2%.

The characteristics of the compound of the invention thus obtained were as follows:

(1) melting point; 205°–206° C. with decomposition measured by Capillary Method.

|  | (2) elementary analysis; | | |
|---|---|---|---|
|  | C (%) | H (%) | N (%) |
| theoretical: | 65.96, | 7.27, | 4.81, |
| experimental: | 65.4, | 7.3, | 4.5. |

(3) IR absorption spectrum; shown in FIGURE.

EXAMPLE 10

Examination of pharmacologic activities and acute toxicity

Pharmacologic activities and acute toxicity of the compound of the invention were examined. Specimens examined are as follows:

Specimen

I; Sodium trans-4-[N-(2'-hydroxybenzylidene)aminomethyl]cyclohexane-1-carboxylate obtained in Example 2, II; Sodium trans-4-[N-(2',3'-dihydroxybenzylidene)aminomethyl]cyclohexane-1carboxylate obtained in Example 4, III; Sodium salt of trans-4-[N-(2',4'-dihydroxybenzylidene) aminomethyl]cyclohexane-1-carboxylic acid obtained in Example 5, IV; Sodium trans-4-[N-(2'-methoxybenzylidene)aminomethyl]cyclohexane-1-carboxylate obtained in Example 6 Comparative Specimen V; indomethacin, VI; homochlorcyclizine.

Comparative Specimens V and VI having the similar pharmacologic activities as the compound of the invention are commercially available in Japan.

The examination was carried out according to the methods described below;

(1) Examination method for inhibitory effect on platelet aggregation

Rabbit platelet rich plasma (PRP) was used for Aggregation Tests. PRP was prepared by centrifugation of blood collected from the ear vein of Rabbit and diluted into number-concentration 300,000/$\mu$l with platelet poor plasma. Platelet aggregation was induced by Sodium Arachidonate and monitored (measured) with a four channel platelet aggregation Tracer PAT-4A (Niko Bioscience Co., Japan). Aggregation Tracer tube containing 230 $\mu$l PRP was preincubated at 37° C. for 5 min with each Specimen.

(2) Examination method for inhibitory effect on polynuclear leukocyte migration

Rat's polynuclear leukocyte migration was examined by Boyden method (refer to Japanese J. Clin. Med., 27(9), 172 (1969)) as follows; a mixture of 10 parts by volume of culture filtrate of E. coli and one part by volume of serum was incubated at 37° C. for one hour and diluted into 5-times volume with physiological salt solution, and the mixture obtained was used as an attractant. After preincubating polynuclear leukocyte suspension with each specimen for 10 min, migration of polynuclear leukocytes was examined.

(3) Examination method for acute toxicity

Acute toxicity was examined by administering perorally an aqueous solution of each Specimen to female JCL-ICR mouse of 5 to 6 weeks after birth.

The results are shown in Table.

TABLE

| Specimen | Platelet aggregation ID$_{100}$ ($\mu$M)[1] | Inhibition rate of polynuclear leukocyte migration (%)[2] | | | | Acute toxicity LD$_{50}$ (mg/kg)[3] |
|---|---|---|---|---|---|---|
|  |  | 1 $\mu$M | 10 $\mu$M | 100 $\mu$M | 1000 $\mu$M |  |
| I | >1000 | 0 | 0 | 39 | 93 | ~2000 |
| II | 120 ~ 60 | 0 | 25 | 66 | 100 | >3000 |
| III | >1000 | 0 | 12 | 42 | 92 | >3000 |
| IV | 400 ~ 500 | 0 | 0 | 27 | 94 | >3000 |
| V | 0.5 ~ 1 | 0 | 0 | 25 | 79 | 30 |
| VI | >1000 | 15 | 48 | 80 | 100 | 350 |

Notes:
[1]The minimum concentration ($\mu$M) of each Specimen for inhibiting completely (100%) the platelet aggregating effect by sodium arachidonate (tested at 400 $\mu$M).
[2]The average value of inhibition rate (%) of polynuclear leukocyte migration at each concentration ($\mu$M) of each Specimen.
[3]Median lethal dose (LD$_{50}$), that is, dose for getting 50% of mice to death, in unit of mg per one kilogram of body weight of mouse.

As shown in Table, the compound of the invention has inhibitory effects on platelet aggregation and polynuclear leukocyte migration, and a low acute toxicity. Accordingly, the compound of the invention can be used as an anti-inflammatory and a remedy for other various diseases.

Furthermore, it is confirmed that sodium salt of trans-4-[N-(3',4'-dimethoxybenzylidene)aminomethyl]cyclohexane-1-carboxylic acid obtained in Example 7, of trans-4-[N-(3',4',5'-trimethoxybenzylidene)aminomethyl]cyclohexane-1-carboxylic acid obtained in Example 8 and of trans-4-[N-(3'-methoxy-4'-hydroxybenzylidene)aminomethyl]cyclohexane-1-carboxylic acid obtained in Example 9 show the similar pharmacologic activities and low acute toxicity.

What is claimed is:

1. A compound represented by the formula (I):

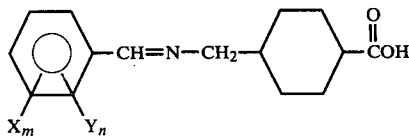 (I)

wherein
 X is hydroxyl- or methoxy group,
 Y is hydrogen or hydroxyl or methoxy group,
 m and n are positive integers and the sum of m and n is equal to or less than 5,
or a pharmaceutically acceptable salt thereof selected from the group consisting of sodium-, potassium-, calcium-, magnesium-, primary ammonium-, secondary ammonium-, tertiary ammonium- and quarternary ammonium salts or a pharmaceutically acceptable alkyl ester thereof having 1 to 3 carbon atoms in said alkyl group, provided that 4-[N-(3′,4′-dihydroxybenzylidene)aminomethyl]cyclohexane-1-carboxylic acid is not included in the formula (I).

2. The compound of claim 1, wherein X is hydroxyl group and Y is hydrogen.

3. The compound of claim 1, wherein X is methoxy group and Y is hydrogen.

4. The compound of claim 1, wherein X is hydroxyl group and Y is methoxy group.

5. Trans-4-[N-(2′-hydroxybenzylidene)aminomethyl]cyclohexane-1-carboxylic acid or a sodium salt thereof.

6. Trans-4-[N-(4′-hydroxybenzylidene)aminomethyl]cyclohexane-1-carboxylic acid.

7. Trans-4-[N-(2′,3′-dihydroxybenzylidene)aminomethyl]cyclohexane-1-carboxylic acid or a sodium salt thereof.

8. Trans-4-[N-(2′,4′-dihydroxybenzylidene)aminomethyl]cyclohexane-1-carboxylic acid or a sodium salt thereof.

9. Trans-4-[N-(2′-methoxybenzylidene)aminomethyl]cyclohexane-1-carboxylic acid or a sodium salt thereof.

10. Trans-4-[N-(3′,4′-dimethoxybenzylidene)aminomethyl]cyclohexane-1-carboxylic acid or a sodium salt thereof.

11. Trans-4-[N-(2′,3′,4′-trimethoxybenzylidene)aminomethyl]cyclohexane-1-carboxylic acid or a sodium salt thereof.

12. Trans-4-[N-(3′-methoxy-4′-hydroxybenzylidene)aminomethyl]cyclohexane-1-carboxylic acid.

13. A pharmaceutical composition in dosage unit form for inhibiting platelet aggregation or polynuclear leukocyte migration comprising an effective amount of at least one compound of claim 1, and a pharmaceutically acceptable carrier or adjuvant.

* * * * *